United States Patent [19]

White

[11] 4,237,911
[45] Dec. 9, 1980

[54] DENTAL PRODUCT

[76] Inventor: Maurice J. E. White, 87 Lewis Rd., Wantirna South, Victoria 3152, Australia

[21] Appl. No.: 35,071

[22] Filed: May 1, 1979

Related U.S. Application Data

[63] Continuation-in-part of Ser. No. 769,655, Feb. 17, 1977, abandoned.

[30] Foreign Application Priority Data

Feb. 18, 1976 [AU] Australia .............................. 4899/76

[51] Int. Cl.³ ............................................. A61C 15/00
[52] U.S. Cl. .................................................... 132/89
[58] Field of Search ........................ 132/89, 93, 91–92; 424/471

[56] References Cited

U.S. PATENT DOCUMENTS 3,078,856  3/1979  Bender et al. ............................ 132/89
4,142,538  3/1979  Thornton ................................ 132/89

FOREIGN PATENT DOCUMENTS 2832005  8/1977  Fed. Rep. of Germany ............. 132/89
2748343  5/1979  Fed. Rep. of Germany ............. 132/89

Primary Examiner—G. E. McNeill
Attorney, Agent, or Firm—Lane, Aitken & Ziems

[57] ABSTRACT

The invention provides a dental product for maintaining oral hygiene which comprises a cellular stem arranged to clean exposed tooth surfaces. The product also comprises a fin for cleaning between adjacent pairs of teeth. It also contains dental fluoride and possibly one or more other agents or reagents such as plaque inhibitors, plaque stain, lavage, breath freshener or mouthwash to combine additional oral hygiene functions in the one product. The product may be chewed to release dental fluoride in optimum amounts for dietary intake and topical application to tooth surfaces.

14 Claims, 8 Drawing Figures

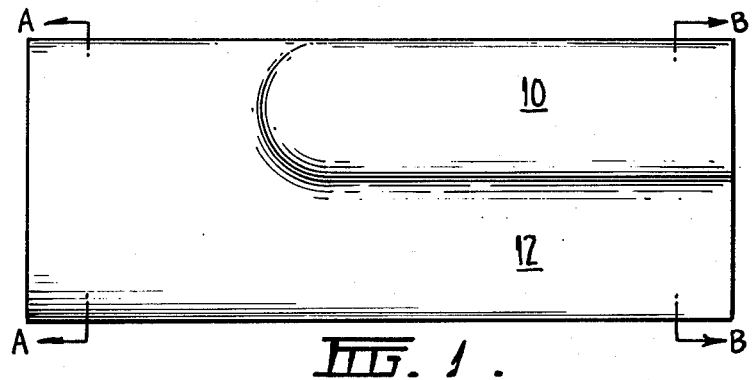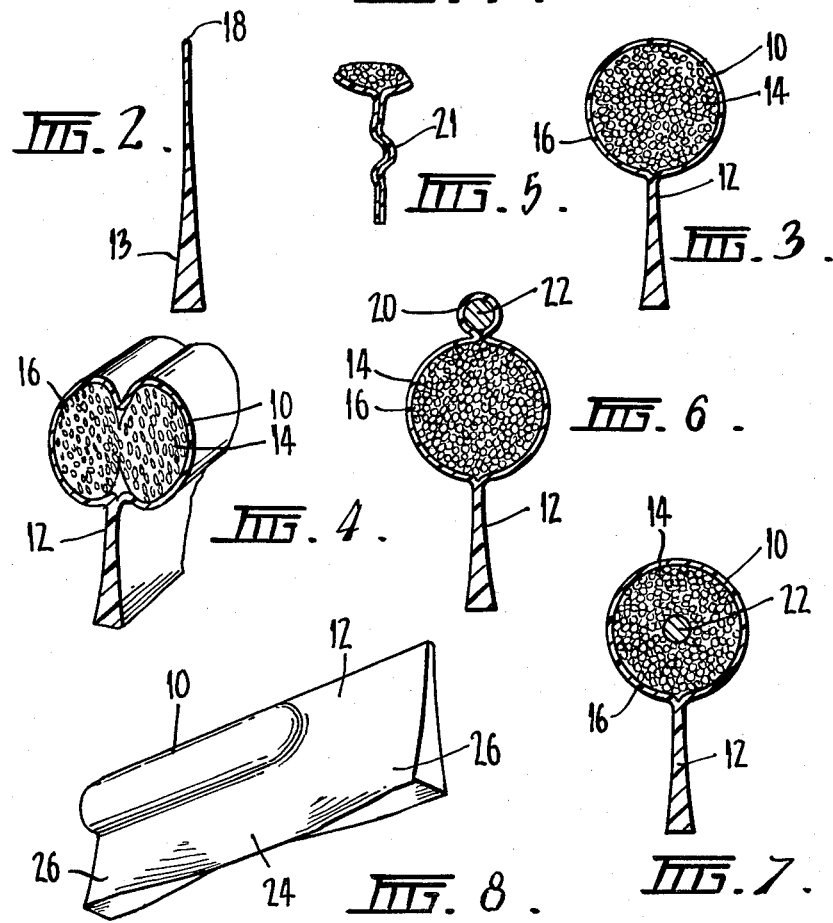

DENTAL PRODUCT

The present application is a continuation-in-part of my copending patent application No. 769655 filed Feb. 17, 1977 now abandoned.

The present invention relates to a dental product which is useful for maintaining oral hygiene and increasing resistance to dental disease.

In order to maintain oral hygiene and increase resistance to dental decay it is necessary to remove plaque, bacteria and food debris from all tooth surfaces to reduce or stop processes which may attack hard tooth tissue and its supporting soft issue. Also it is desirable to provide a means for supplying on a daily basis dental fluoride in optimum amounts for both dietary intake, particularly in the case of children while teeth are developing, and topical application to tooth surfaces to increase resistance to such attack.

The toothbrush is currently the mainstay of oral hygiene devices and the only form of device with standards in a number of countries although some countries have standards for toothpaste to be used in conjunction with the toothbrush. Other oral hygiene devices have been proposed but have not gained wide acceptance. However, it is generally accepted that the toothbrush cannot clean between teeth nor can it clean the occlusal pits and fissures of posterior teeth. Thus, the supplemental use of dental floss is often recommended to attempt to attain the degree of mechanical plaque control necessary to prevent dental caries of the teeth forming as well as disease of the gum. Hitherto there has been no effective way of cleaning pits and fissures.

It has been found that the toothbrush, dental floss, toothpicks and other oral hygiene devices all require a degree of rigidity and must be placed under tension to enable the active part to be pushed against the tooth surface in order to remove plaque. A number of passes are necessary to effect this because the toothbrush, for example, can only concentrate between 1000 and 4000 bristles per cm² depending on diameter. Further, the bristles tend to spread during use so that they have a streaky cleaning action.

The product of the present invention has the advantage that it is capable of efficiently cleaning all tooth surfaces and delivering fluoride in optimum amounts for dietary intake and topical application.

In accordance with the present invention there is provided a dental product for maintaining oral hygiene comprising:

an elongated, chewable stem formed of a resilient thermoplastic cellular material for cleaning tooth surfaces; said cellular material having a density of from about 0.005 to about 0.5 g/cm³;

an elongated fin of the thermoplastic material formed integrally with said stem and extending laterally from the periphery of said stem along the entire length of the stem, said fin being arranged to be inserted through the contact points between adjacent pairs of teeth and drawn lengthwise between said adjacent teeth in close engagement with the proximal surfaces of said teeth to thereby clean said proximal surfaces and the interproximal space between said teeth;

a dental fluoride disposed within closed cells of the thermoplastic cellular material in an amount of 1 mg of fluoride (measured as fluoride ion) per volume of cellular material in the range of about 2 cm³ to about 12 cm³, preferably about 3 cm³ to about 10 cm³; said fluoride being substantially evenly distributed throughout the cellular material and being in the form of a plurality of discrete units; and an outer skin extending around said stem and said fin which is broken after the fin has been used to clean between said teeth to expose the thermoplastic cellular material of said stem and to release said fluoride for topical application to said teeth and fluoride dietary intake.

In use, the fin is inserted through the contact points between adjacent pairs of teeth and drawn lengthwise between said teeth in close engagement with the proximal surfaces to remove plaque and other material threfrom to thereby clean said proximal surfaces and the interproximal space therebetween. The fin is preferably of such depth as to contact and depress the dental papilla between the teeth to stimulate the papilla. Stimulation of the dental papilla improves the tone of the gums and reduces the size of the gingival crevice so reducing the possibility of plaque and other material entering the gingival crevice.

The fin may be corrugated to enable it to be inserted through the contact points and to spring back into close engagement with the proximal surface. However, it requires two handed operation to insert such a fin between the contact points. Therefore, the fin preferably has a thin portion which is inserted through the contact points and at least one thick portion which is drawn lengthwise between said adjacent teeth in close engagement with the proximal surfaces. The thin portion may be located at any point on the fin including an extension thereof which is described below, but is preferably located adjacent the mid-point of the stem. The thick portion may be formed of cellular material as an extension of the cellular material of the stem. A cellular thick portion has the necessary resiliency to closely engage the proximal surfaces. Also the thick portion preferably has a triangular section to provide the best fit with the triangular embrasure forming the interproximal space between adjacent pairs of teeth.

Subsequently to the use of the fin, the protective skin around the cellular stem is broken to expose the cellular thermoplastic material. This may be done by breaking the stem in half and bending back the broken halves on a residual connected portion of the skin to present a double thickness of cellular material. The stem may be held between forefinger and thumb and the cellular material rubbed against front and back tooth surface to remove plaque and other material threfrom. Also, the gums adjacent these surfaces are simultaneously stimulated by contact with the cellular material. Therefore a cellular material having a density of from about 0.005 to about 0.5 g/cm³, preferably about 0.01 to about 0.05 g/cm³, enables the tooth surfaces to be exposed to a larger number of fibres formed by the cell walls of the cellular material such as from 10,000 to 10 million e.g. about 20000/cm² for a cellular material having a density of about 0.013 g/cm³. This gives a far more efficient cleaning action than that provided by a toothbrush and enables material to be removed from tooth surfaces including irregular surfaces, in one wipe using hand pressure.

Then, the product is chewed into small pieces between posterior teeth which action cleans the occlusal surfaces particularly the pits and fissures thereof. Simultaneously, the dental fluoride is released and provides both otpimum topical application and dietary intake. The rate of the release of fluoride needs to be controlled to give a concentration of fluoride in the range of 100 to 1000 ppm fluoride ion in the saliva of the mouth. In this concentration range the fluoride causes remineralisation of the tooth enamel which has been dissolved by acids of the mouth. Further the remineralisation is in the form of the mineral fluorapatite which has a very low solubility in mouth fluids. If the rate of release is uncontrolled and higher fluoride concentrations are obtained, remineralisation takes place but the mineral formed is calcium fluoride which is much more soluble from fluorapatite and is therefore dissolved away quite easily.

In accordance with the present invention it has been found that the desired controlled rate of release can be obtained by incorporating the fluoride in closed cells of the cellular material in an amount of 1 mg of fluoride (measured as fluoride ion) to about 3 $cm^3$ to about 10 $cm^3$ of cellular material, and substantially evenly distributing the flouride throughout the cellular material in the form of a pluorality of discrete units. The discrete units may be solid particles or droplets of fluoride in aqueous solution. The units may be incorporated in a thermoplastic melt as will be described hereafter.

The cellular material should have an essentially closed cell structure although it may have a minor proportion of open cells. Typically, the thermoplastic material is polystryene, polypropylene, polyethylene, polyurethane, polyvinyl chloride or a copolymer thereof, cellulose acetate or polyethyl vinyl acetate or a copolymer.

Preferred fluoride materials are sodium fluoride or sodium monofluorophosphate although any dental fluoride material can be used if desired. The fluoride material may be incorporated in the cellular stem in solid form or in the form of an aqueous solution. Some water is always mixed with the fluoride to be sure it is not encapsulated in such a way as to make it not available. Since the cellular stem has a closed cell structure each cell must be ruptured to release the fluoride material.

The use of a solid fluoride material gives a slower rate of release and greater control over the rate of release which features are desired in products of the invention intended for use in areas with fluoridated water supplies.

Optionally, the dental product of the present invention may contain flavouring materials, materials which freshen breath or mouth wash.

Also, a plaque staining agent may be incorporated in the dental product of the present invention. Typically, an erythrocine dye is used but any plaque staining agent can be used if desired.

It is preferred to incorporate the plaque staining agent where this is used, in a separate unit or in a particular regions within the stem. This can be done by providing a separate cell structure extending laterally and externally of the cellular stem and attached thereto by any suitable means such as an extension of the outer protective skin. Alternatively, the plaque staining agent could be incorporated in a region within the cellular stem and extending along the length thereof.

Alternatively, the dental product of the present invention may contain a plaque inhibiting agent. Typically, chlorhexidrene is used for this purpose but any plaque inhibiting agent can be used, if desired. The plaque inhibiting agent, where it is used, can conveniently be incorporated into the dental product in a manner similar to that described above for plaque staining agents.

Other oral hygiene products may be incorporated in the dental product of the present invention, if desired.

It is preferred to manufacture the product of the present invention by injection moulding or extrusion of a thermoplastic foam as in a mould or through a set of rollers which give the desired shape and also forms the skin and fin.

The foam itself can be manufactured in known manner by incorporation of a blowing agent which can be water, into the plastics material prior to extrusion.

The agents or reagents can be incorporated into the foam in a number of ways depending on the physical and chemical properties of the ingredients and the temperature and pressures involved. For example, a dental fluoride can be mixed with a thermoplastic melt prior to moulding extrusion in the form of a saturated aqueous solution. Alternatively, the fluoride can be admixed with a thermoplastic melt as a solid in the form of an aqueous slurry. The presence of some water ensures that the fluoride is not encapsulated within the plastics material but is contained in the cells of the foam. This is necessary for the fluoride to be readily available to a user.

The invention will now be described by way of example with reference to the accompanying drawings, in which:

FIG. 1 is a side elevation of a dental product in accordance with the present invention;

FIG. 2 is a section along the line A—A as shown in FIG. 1 showing the construction of a fin;

FIG. 3 is a section along the line B—B as shown in FIG. 1, showing the construction of a cellular stem;

FIG. 4 is an end elevation of the dental product of FIG. 1 in broken open condition;

FIG. 5 is an end elevation of a fin having an alternative construction to that shown in FIG. 2;

FIG. 6 is a view similar to FIG. 3 showing a dental product with a separate cell structure from the cellular stem, and containing a plaque stain or plaque inhibitor;

FIG. 7 is a view similar to FIG. 3 showing a dental product containing a plaque stain or plaque inhibitor in the centre of the cellular stem; and FIG. 8 is an underneath perspective view of the dental product of FIG. 1 showing the fin with thin and thick portions.

In FIGS. 1 to 3, there is shown a dental product comprising a cellular stem 10 and a thin fin 12. As shown the fin 12 extends beyond the length of the stem 10, the extending fin portion being of increased width such that the product has an overall rectangular configuration. This is so the product can clean proximal surfaces of adjacent pairs of teeth which are very long.

As can be seen in FIG. 3 the cellular stem 10 is circular in cross-section and has the shape of a cigarette or toothpick. Typically, the dental product is about 60 mm long and about 12 mm wide, the stem having a diameter of about 6 mm.

The cellular stem 10 is formed from a foamed thermoplastic material and contains a plurality of closed cells 14. However, the cells do not extend to the periphery of the stem 10, there being an integral outer protective skin 16 around the periphery of the stem 10. This ensures that any agents or reagents contained in the cells are not inadvertently released.

As can be seen in FIG. 2, the fin 12 is tapered upwardly and has a generally triangular portion 13 to enable it to fit into the triangular embrasures found between adjacent pairs of teeth. Typically, the fin has a width of about 0.002" at its narrowest portion 18.

The dental product is utilized by a user inserting the fin between pairs of teeth in the manner of a toothpick or dental floss. The fins generally triangular or corrugated shape enables it to closely engage with the edges of adjacent teeth and remove food debris from therebetween and dental plaque therefrom. Then the cellular stem can be cut or broken open and folded back on itself using a residual connection portion of the skin 16 as a hinge. This presents a double thickness cellular surface (see FIG. 4) to the user who holds the two loose ends in the fingers or clips them in a handle and then applies the cellular surface to the exposed areas of his or her teeth usually after a meal, to clean the same and remove food debris and dental plaque therefrom. The fin does not break in this direction and provides a harder point to remove stubborn debris from the teeth. Subsequently the product is chewed to clean occlusal surfaces of posterior teeth and release the agents or reagents, particularly the dental flouride.

An alternative construction of the fin 12 is shown in FIG. 5, wherein it is transversely corrugated at 21 to provide a close fit between adjacent teeth. The fin 12 may be also used for cleaning under dental bridges and may be arranged to be broken away from the stem 10 for this purpose.

It should be noted that although the edge of the fin remote from the stem need not be rectilinear, it should not be serrated as a serrated edge would be likely to cause damage to the papilla instead of the beneficial stimulation provided by the device of the present invention.

In FIG. 6 there is shown a dental product similar to that shown in FIGS. 1 to 3 and containing a separate cell structure 20 extending laterally of and attached to the cellular stem 10 by an extension of the skin 16. The separate cell structure 20 contains a plaque inhibitor or plaque stain 22. The separate cell structure may be arranged to be broken away from the cellular stem 10.

In FIG. 7 there is shown a dental product similar to that shown in FIGS. 1 to 3 containing a plaque inhibitor or plaque stain 22 within the cellular stem 10. The plaque inhibitor or plaque stain 22 is preferably incorporated into the dental product by injection during or after manufacture.

In FIG. 8 it can be seen that the fin 12 comprises a thin portion 24 having a thickness of about 0.025 mm so that it can be inserted through the contact points between adjacent pairs of teeth. The thin portion 24 is located approximately adjacent to the mid point of the stem 10. On each side of the thin portion 24 the fin has a thick portion 26 of cellular material and of sufficient thickness and resilience to closely engage the proximal surfaces of teeth as the fin is drawn therebetween.

It will be apparent that my invention provides an oral hygiene device having a unique combination of useful features. A particularly important feature is its ability to penetrate very small pits and fissures. The significance of this feature is emphasised by the fact that a space the size of a pinhead can contain as many as 33 million bacteria. When the device is chewed to penetrate the pits and fissures on the tops of posterior teeth under high compressive pressure (e.g. 200 lbs/in$^2$), this has excellent scouring action to remove plaque and retard its regeneration. The plaque and bacteria are swallowed and denatured by gastric juices and if in sufficient numbers will stimulate the antibody reaction of the saliva and gingival fluids.

The invention will now be illustrated by the following Examples.

EXAMPLE 1

A slurry containing 3.3 grams of solid, particulate sodium fluoride in admixture with 10 ml of water is mixed with 1 kg of low density polyethylene which has previously been mixed with 1% by weight of "Geritron" Ac/4 which is a blowing agent.

The mixture is initially fed into an unheated feed zone of an extruder. The feed zone has a length of about 2-3 diameter. The extruder has a length to diameter ratio greater than 18:1 and compressive ratio greater than 5:1 while maintaining a minimum head pressure of 1500 psi and a die temperature of 220° C. The head temperature is maintained at 215° C., the metering zone temperature at 200° C. and the remainder of the extruder at 165° C. The die may be plane or circular in configuration.

The extrudate foams on leaving the die to produce a cellular foam having a density of about 0.013 g/cm$^3$ and containing 1 mg of fluoride per 4 cm$^3$ of foam. The foamed extrudate is hauled off by rotating rollers which rotate at a speed such that the extrudate is placed under tension, and is pressed to the desired shape by being passed through externally water chilled embossing rollers at about 40° C., wherein it is pressed into individual dental products as shown in FIG. 1 or into a sheet containing alternating cellular stem portions and fin portions from which individual units can be torn. The passage through the rollers forms the outer protective skin and shapes the product including the thin portion of the fin. Further, the hauling off process ensures that the fin can be readily torn longitudinally but not laterally. Initially, the foam is open celled but the hauling off process closes most of the cells.

Preferably, the fluoride level is adjusted to provide a level of dental fluoride of about 0.33 mg per oral hygiene unit. If one unit is used and chewed in its entirety after each meal of the day by a user this gives a daily fluoride dietary intake of 1 mg.

Agents such as chlorhexidrene and erythrocine dye are preferably injected into the units in aqueous solution during post extrusion operations just before the rollers.

EXAMPLE 2

Using a precedure similar to Example 1 a dental product in accordance with the present invention was produced from the following composition:
 95 grams particulate polyethyl vinyl acetate (PEVA)
 4.1 grams solid particulate sodium fluoride
 0.5 grams particulate sodium bicarbonate
 0.4 grams particulate citric acid
 1 ml water
 1 ml oil of peppermint The water is admixed with the PEVA to wet the surface of the plastic. Sodium fluoride is then admixed to wet the surface of the fluoride. The remaining components are then admixed. The mixture is passed into an extruder through a metering zone and at a point of greater flight depth after the metering zone the mix is a hormogerized mass. Freon gas at a higher pressure than that of the melt is passed into the the mass as blowing agent. The mass is then passed through a further metering zone to evenly distribute the freon throughout the melt. Following extrusion the melt is blown out about 70 times to a density of about 0.015 g/cm$^3$ and contains 1 mg of fluoride per 4 cm$^3$ of cellular material. Preferably, the rollers are shaped so that the stem portion of each product is not stretched but the fin portion is stretched as the product passes through the rollers. The stretching imparts strength to the fin, particularly at the thin portion thereof so that it is more resistant to tearing in use whilst the stem can be easily ruptured for release of fluoride and other materials.

The foam in sheet form may be used for packaging candy or other food to enable people to clean teeth after eating.

The cleaning power of chewing gum may be improved by incorporation of particles of foam according to the invention.

I claim:

1. A dental product for maintaining oral hygiene comprising:

an elongated, chewable stem formed of a resilient thermoplastic cellular material for cleaning tooth surfaces; said cellular material having a density of from about 0.005 to about 0.5 g/cm$^3$;

an elongated fin of the thermoplastic material formed integrally with said stem and extending laterally from the periphery of said stem along the entire length of the stem, said fin being arranged to be inserted through the contact points between adjacent pairs of teeth and drawn lengthwise between said adjacent teeth in close engagement with the proximal surfaces of said teeth to thereby clean said proximal surfaces and the interproximal space between said teeth;

A dental fluoride disposed within cells of the thermoplastic cellular material in an amount of 1 mg of fluoride ion per volume of cellular material in the range of about 2 cm$^3$ to about 12 cm$^3$, said fluoride being substantially evenly distributed throughout the cellular material and being in the form of a plurality of discrete units; and an outer skin extending around said stem and said fin which is broken after the fin has been used to clean between said teeth to expose the thermoplastic cellular material of said stem and to release said fluoride for topical application to said teeth and fluoride dietary intake.

2. A dental product as defined in claim 1 wherein the amount of fluoride ion is 1 mg per volume of cellular material in the range of about 3 cm$^3$ to about 10 cm$^3$.

3. A dental product as defined in claim 1 or 2 wherein the fin is tapered to provide a thin portion which is inserted through the contact points between adjacent pairs of teeth and a thick portion which is then drawn lengthwise between said adjacent teeth in close engagement with the proximal surfaces of said teeth to evenly clean said proximal surfaces and the interproximal space between said teeth.

4. A dental product as defined in claim 3 wherein the thin portion is located intermediate adjacent thicker portions of the fin.

5. A dental product as defined in claim 4 wherein the thin portion has a minimum thickness of about 0.025 mm.

6. A dental product as defined in claim 1 or 2 wherein the cellular material has a density of from 0.01 to 0.05 g/cm$^3$.

7. A dental product as defined in claim 1 or 2, wherein the fin extends beyond the length of said stem, said extending fin portion being of increased width such that said product has an overall rectangular configuration.

8. A dental product as defined in claim 1 or 2, further comprising an oral hygiene agent disposed within the thermoplastic cellular material of said stem.

9. A dental product as defined in claim 8, wherein said agent is a plaque inhibiting agent.

10. A dental product as defined in claim 8, wherein said agent is a plaque staining agent.

11. A dental product as defined in claim 1 or 2, further comprising an additional stem of said thermoplastic material extending laterally and externally of said elongated stem.

12. A dental product as defined in claim 11, wherein said additional stem contains a plaque inhibiting agent.

13. A dental product as defined in claim 11, wherein said additional stem contains a plaque staining agent.

14. A dental product as defined in claim 1 or 2, wherein said thermoplastic material of said stem and fin is polyethylene, polypropylene, polystyrene, polyvinyl chloride or a copolymer thereof, polyurethane, cellulose acetate or polyethylvinyl acetate.

* * * * *